United States Patent
Sablone

(10) Patent No.: US 12,064,324 B2
(45) Date of Patent: Aug. 20, 2024

(54) METHOD AND APPARATUS FOR PRODUCING ABSORBENT SANITARY ARTICLES AND RELATIVE ABSORBENT SANITARY ARTICLE

(71) Applicant: Fameccanica.Data S.p.A., San Giovanni Teatino (IT)

(72) Inventor: Gabriele Sablone, Pescara (IT)

(73) Assignee: Fameccanica.Data S.p.A.

( * ) Notice: Subject to any disclaimer, the term of this patent is extended or adjusted under 35 U.S.C. 154(b) by 630 days.

(21) Appl. No.: 17/075,806

(22) Filed: Oct. 21, 2020

(65) Prior Publication Data
US 2021/0121334 A1    Apr. 29, 2021

(30) Foreign Application Priority Data
Oct. 25, 2019   (IT) .................. 102019000019785

(51) Int. Cl.
A61F 13/15   (2006.01)
A61F 13/496   (2006.01)

(52) U.S. Cl.
CPC .. *A61F 13/15658* (2013.01); *A61F 13/15723* (2013.01); *A61F 13/496* (2013.01)

(58) Field of Classification Search
CPC .......... A61F 13/15658; A61F 13/15723; A61F 13/496; A61F 13/49061
See application file for complete search history.

(56) References Cited

U.S. PATENT DOCUMENTS

| | | | |
|---|---|---|---|
| 10,059,015 B2* | 8/2018 | Schneider | A61F 13/00 |
| 10,188,560 B2* | 1/2019 | Mueller | A61F 13/565 |
| 10,342,711 B2* | 7/2019 | Tomioka | A61F 13/15804 |
| 10,517,779 B2* | 12/2019 | Barna | A61F 13/49011 |
| 2012/0065043 A1* | 3/2012 | Lam | A61F 13/15804 493/344 |
| 2017/0105882 A1* | 4/2017 | Sablone | A61F 13/15658 |
| 2018/0271713 A1* | 9/2018 | Tomioka | A61F 13/15723 |
| 2019/0008703 A1* | 1/2019 | Saito | A61F 13/565 |

FOREIGN PATENT DOCUMENTS

| | | | | |
|---|---|---|---|---|
| EP | 1875819 A1 | 1/2008 | | |
| WO | WO-2012098013 A1 * | 7/2012 | ....... | A61F 13/15585 |
| WO | 2013168753 A1 | 11/2013 | | |
| WO | WO-2018123154 A1 * | 7/2018 | ............ | A61F 13/49 |

OTHER PUBLICATIONS

European Search Report dated Jul. 1, 2020. 8 pages.

* cited by examiner

*Primary Examiner* — Guy K Townsend
*Assistant Examiner* — Peter Daniel Smith
(74) *Attorney, Agent, or Firm* — RMCK Law Group PLC

(57) ABSTRACT

A method and apparatus for producing absorbent sanitary articles according to a Machine Direction technique, each sanitary article having an absorbent body, a front waistband and a rear waistband having different lengths from each other.

1 Claim, 3 Drawing Sheets

METHOD AND APPARATUS FOR PRODUCING ABSORBENT SANITARY ARTICLES AND RELATIVE ABSORBENT SANITARY ARTICLE

CROSS-REFERENCE TO RELATED APPLICATION

This application claims priority to Italian Patent Application No. 102019000019785 filed Oct. 25, 2019. The disclosure of the above application is incorporated herein by reference in its entirety.

FIELD OF THE INVENTION

The present invention relates to a method and an apparatus for producing absorbent sanitary articles.

The invention was developed with particular regard to producing absorbent sanitary articles that can be worn as pants, for example, the so-called training pants. The invention is applicable both for producing permanently closed-type absorbent sanitary articles and those of the openable and reclosable-type.

The present invention relates, in particular, to a method and an apparatus for producing absorbent sanitary articles according to the so-called "Machine Direction" production technique.

DESCRIPTION OF THE PRIOR ART

Absorbent sanitary articles known as "training pants" are normally formed by an absorbent body having an elongated shape along a longitudinal axis and two transverse waistbands (a front waistband and a rear waistband) applied to opposite ends of the absorbent body on the surface that, during use, faces towards the clothing. The transverse waistbands may be elasticized and can be attached to each other permanently or by opening and reclosable closing formations.

For producing absorbent sanitary articles composed of an absorbent body of elongated shape and two transverse waistbands, a production technique called "Cross Direction" is normally used, which consists in forming two continuous parallel sheets, forming the front and rear waistbands, which advance in a machine direction and applying the absorbent bodies between the continuous sheets. The absorbent bodies are oriented transversely with respect to the machine direction and are attached at their opposite ends to the continuous sheets forming the waistbands.

It is known that using this production technique the absorbent bodies are not always applied in a precise way and protrude with respect to the waistbands. In the latter case, a cut is made to eliminate the protruding portion, which involves scraps and requires appropriate cutting devices equipped with scrap-removal units.

In the case that absorbent bodies are applied to the continuous sheets by gluing, it is known that glue is present on the protruding portion of the absorbent bodies to be removed. The presence of glue on the part to be removed further complicates the cutting and removal of the scrap. Examples of methods for producing absorbent sanitary articles according to the Cross Direction technique are described in documents EP-A-1013251, IT1379452, IT1410464 and IT1410465 by the same Applicant.

The Cross Direction production technique makes it possible to produce absorbent sanitary articles wherein the absorbent body is shorter than the overall length of the finished product, i.e. with the outer edges of the waistbands protruding beyond the transverse edges of the absorbent bodies.

However, with the Cross Direction production technique, it would be very complex to produce absorbent sanitary articles wherein the two waistbands have different lengths, for example, with the rear waistband having a longer length than the front waistband, so that the closing formations are placed on the front of the user instead of on the sides. In the case wherein it is required to produce absorbent sanitary articles with front and rear waistbands with different lengths with the Cross Directions production technique, it would be necessary to use very complex equipment with a high production of scraps.

OBJECT AND SUMMARY OF THE INVENTION

The present invention aims to provide a method and apparatus for producing absorbent sanitary articles that overcome the problems of the prior art.

In particular, the present invention aims to provide a method and an apparatus that allow the production of absorbent sanitary articles without scraps, composed of an absorbent body with an elongated shape, and two waistbands with different lengths.

According to the present invention, this object is achieved by a method having the characteristics forming the subject of claims 1 and 5.

According to another aspect, the present invention relates to an absorbent sanitary article having the characteristics forming the subject of claim 8.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein.

It will be appreciated that the various figures may not be represented on the same scale.

DETAILED DESCRIPTION

Figure 1:
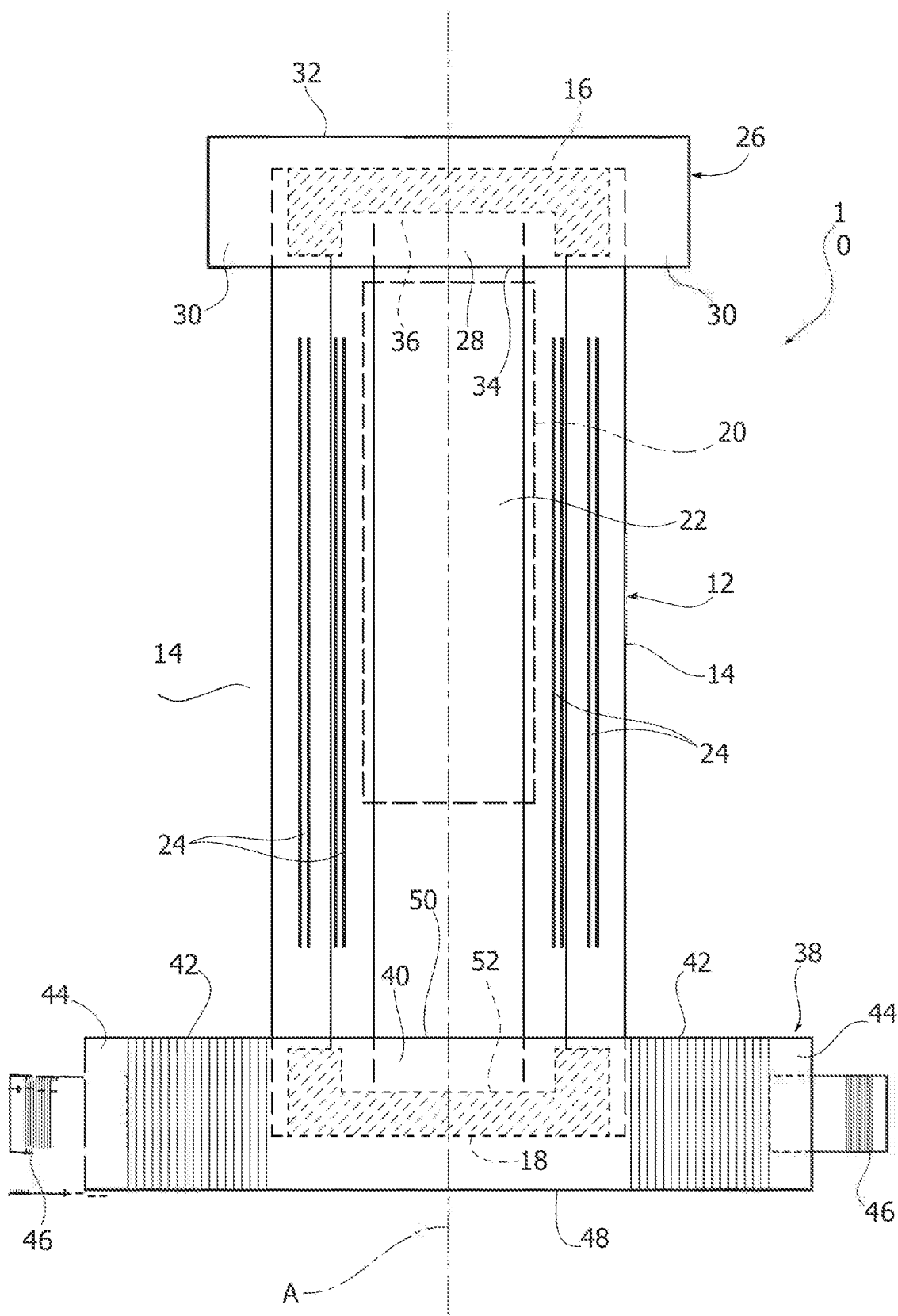
FIG. 1 is a plan schematic view of an embodiment of an absorbent sanitary article according to the present invention.

With reference to FIG. 1, numeral 10 indicates an absorbent sanitary article illustrated in an open and extended position. The absorbent sanitary article 10 illustrated—by way of example—in FIG. 1 is an openable and reclosable training pant. However, it is understood that the present invention may also apply to absorbent sanitary articles of another type, for example, incontinence pads for adults either permanently closed or not.

The absorbent sanitary article 10 comprises an absorbent body 12 having an elongated shape along a longitudinal axis A. The absorbent body 12 has two longitudinal sides 14 that extend along a direction defined by the longitudinal axis A. The longitudinal sides 14 may be parallel to the longitudinal axis A. The absorbent body 12 has a front transverse side 16 and a rear transverse side 18 transverse to the longitudinal axis A. The front transverse side 16 and/or the rear transverse side 18 may be perpendicular to the longitudinal axis A.

The absorbent body 12 comprises an absorbent core 20 enclosed between an inner sheet of liquid-permeable material (topsheet) and an outer sheet of impermeable material (backsheet). For example, the absorbent core 20 may be sandwiched between the inner sheet and the outer sheet. Additional absorbent layers may be comprised between the inner sheet and the outer sheet of the absorbent core 20 such as, for example, an Acquisition Diffusion Layer, commonly referred to as ADL. The topsheet has a surface intended to face, during use, towards the user's body. This topsheet surface is indicated in the drawings with the reference 22 and refers to the inner surface of the absorbent body 12.

The absorbent body 12 may comprise additional components as is customary in the field, such as, for example, elastic elements for the legs 24 (leg cuffs) applied on the inner surface 22 and extending parallel to the longitudinal axis A, and/or diffusion layers of the liquids, etc.

The absorbent sanitary article 10 comprises a front waistband 26 having an elongated shape in a transverse direction. In the embodiment illustrated in the figures, the front waistband 26 may be formed by a non-elastic sheet, for example, a sheet of non-woven fabric. The front waistband 26 has a central portion 28 attached to the inner surface 22 of the absorbent body 12, and two side portions 30 which extend in a transverse direction outwardly with respect to the longitudinal sides 14 of the absorbent body 12. The front waistband 26 has an outer transverse edge 32 and an inner transverse edge 34. Along the longitudinal axis A, the outer transverse edge 32 extends outwardly with respect to the front transverse side 16 of the absorbent body 12.

In a possible embodiment, the front waistband 26 may be attached to the inner surface 22 of the absorbent body 12 along a front attachment area 36 having a "C" shape facing the center of the absorbent body 12. The attachment area 36 may be formed of a layer of adhesive. In the example illustrated in the Figures, the front attachment area 36 has a central zone with the shape of an elongated rectangle in the transverse direction, and adjacent to the front transverse side 16 of the absorbent body 12, and two side areas having the shape of elongated rectangles in the longitudinal direction, and adjacent to the longitudinal sides 14 of the absorbent body 12. This arrangement of the attachment area 36 allows a pocket to be formed between the central portion 28 of the front waistband 26 and the inner surface 22 of the absorbent body 12, open along the inner transverse edge 34 of the front waistband 26. This pocket, during use, may be useful for containing feces.

The absorbent sanitary article 10 comprises a rear waistband 38 having an elongated shape in a transverse direction. The rear waistband 38 has a central portion 40 attached to the inner surface 22 of the absorbent body 12, and two side portions 42 which protrude in a transverse direction outwardly with respect to the longitudinal sides 14 of the absorbent body 12.

The rear waistband 38 has a greater dimension in the transverse direction than the dimension in the transverse direction of the front waistband 26.

In a possible embodiment, the central portion 40 of the rear waistband 38 is not elasticized, and the side portions 42 are at least partly elasticized and elastically extendable in the transverse direction. The side portions 42 may have non-elasticized end regions 44 on which openable and reclosable closing formations 46 can be attached, which are configured to cooperate with the outer surfaces of the side portions 30 of the front waistband 26.

The rear waistband 38 has an outer transverse edge and an inner transverse edge 50. Along the longitudinal axis A, the outer transverse edge 48 extends outwardly with respect to the rear transverse side 18 of the absorbent body 12.

In a possible embodiment, the central portion 40 of the rear waistband 38 is attached to the inner surface 32 of the absorbent body 12 along a rear attachment area 52 having a "C" shape facing the center of the absorbent body 12. The rear attachment area 52 may have a specular shape with respect to the front attachment area 36. The rear attachment area 52, may also have a central zone with the shape of an elongated rectangle in the transverse direction and adjacent to the rear transverse side 18 of the absorbent body 12, and two side areas having the shape of elongated rectangles in the longitudinal direction and adjacent to the longitudinal sides 14 of the absorbent body 12. In this case as well, a pocket may be formed between the central portion 40 of the rear waistband 38 and the inner surface 22 of the absorbent body 12, open along the inner transverse edge 50 of the rear waistband 38. The rear pocket may also be useful, in use, for collecting feces.

The absorbent sanitary article 10 has an overall length in the direction of the longitudinal axis A greater than the length of the absorbent body 12. The front and rear waistbands 26, 38 are applied to the inner surface of the absorbent body 12 over the transverse sides 16, 18. This avoids direct contact of the transverse edges 16, 18 of the absorbent body 12 with the user's skin, which could cause irritation.

The front and rear waistbands 26, 38 have different lengths and can be made of different materials. For example, in the illustrated embodiment, the front waistband 26 may have a transverse dimension smaller than the transverse dimension of the rear waistband 38, so that closing the absorbent sanitary article 10 can be carried out on the front of the user instead of on the sides.

In a possible embodiment, the absorbent body 12, the front waistband 26 and the rear waistband 38 may have rectangular shapes.

According to possible embodiments, the absorbent sanitary article 10 may comprise a connecting panel (frontal tape) configured to couple with the opening and closable closing formations 46. The connecting panel is provided with a connecting surface configured to couple with the openable and reclosable closing formations 46, and an attachment surface opposite the connecting surface attached to the front waistband 26 and the surface of the back sheet.

With reference to FIGS. 2-9, a possible embodiment of a method and an apparatus for producing an absorbent sanitary article 10 of the type illustrated in FIG. 1 will now be described.

The method initially envisages the provision of a continuous absorbent composite web 60 (FIG. 3) having a longitudinal axis A and formed by a continuous succession of blanks of absorbent bodies. The continuous absorbent composite web 60 comprises an inner sheet of liquid-permeable material and an outer sheet of impermeable material, between which a continuous succession of absorbent cores 20 are enclosed, arranged with their respective longitudinal axes aligned with the longitudinal axis A, and spaced apart from each other in the longitudinal direction.

The continuous composite web 60 is produced according to the Machine Direction technique, in a manner well known in the sector of producing absorbent articles.

Figure 2:
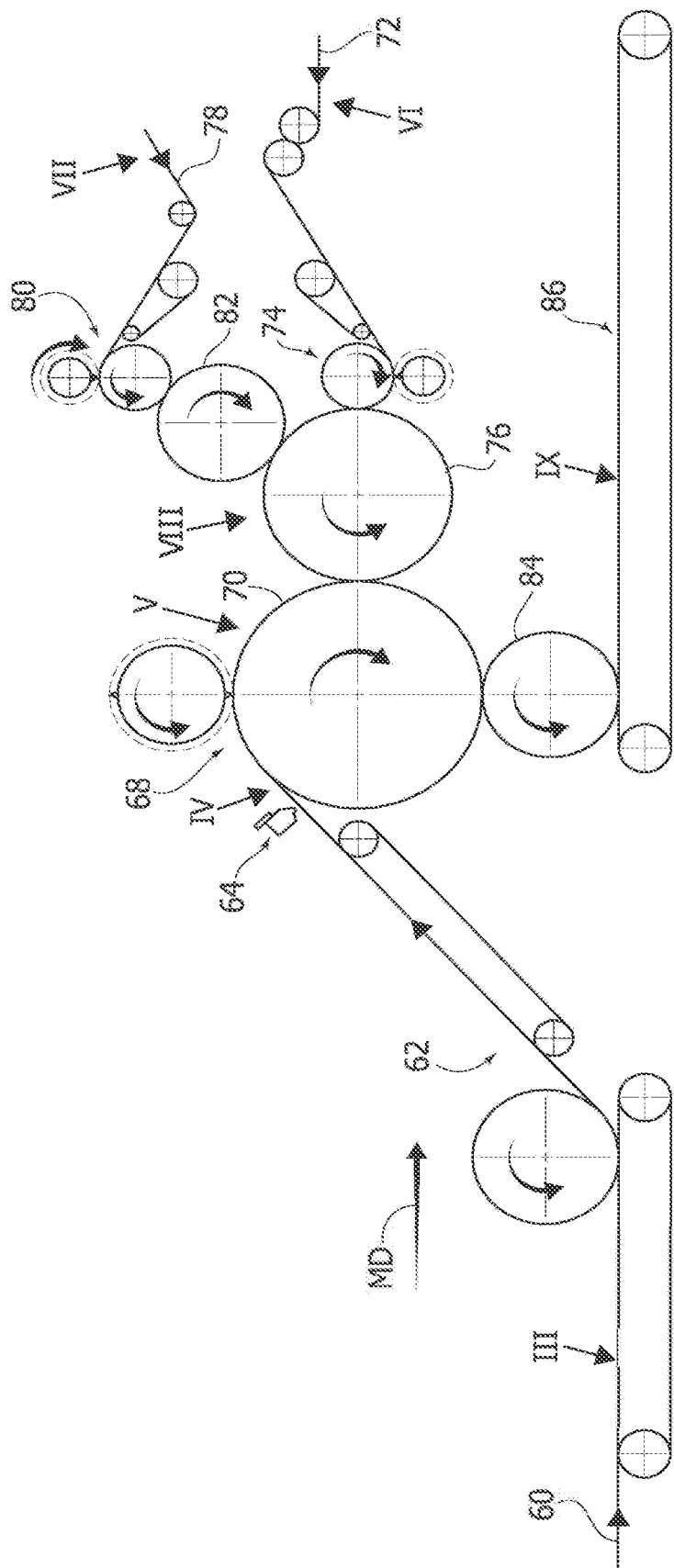
FIG. 2 is a schematic side view of an embodiment of an apparatus configured for producing absorbent sanitary articles shaped as illustrated in FIG. 1.
Figure 3:
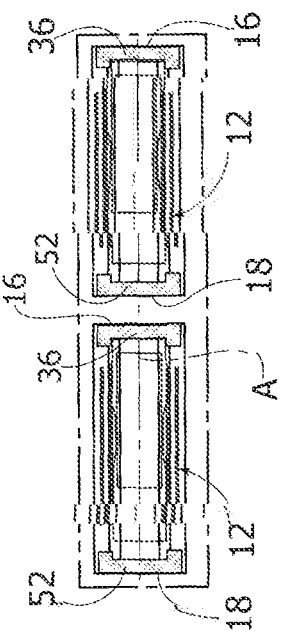
FIGS. 3-9 are plan views illustrating the steps of a method for producing absorbent sanitary articles corresponding to the cross-sections of the apparatus indicated by arrows III-IX of FIG. 2.
Figure 4:
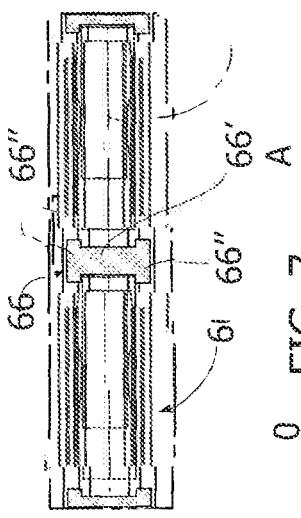

Referring to FIG. 2, the continuous absorbent composite web 60 is advanced along a machine direction MD along a transport unit 62.

A glue application unit 64 applies glue areas 66 (FIG. 4) on the inner surface of the absorbent continuous composite web 60, said areas being spaced apart in the direction of the longitudinal axis A. Each glue area 66 has an "I" shape, with a central zone 66' elongated in the transverse direction and two side areas 66" wider than the central zone.

Figure 5:
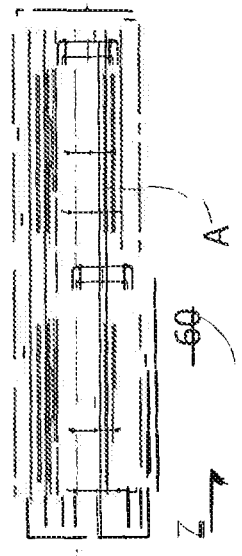

After applying the glue, the continuous absorbent composite web 60 is cut along a transverse direction perpendicular to the longitudinal axis A in a cutting unit 68. At the outlet of the cutting unit 68, the continuous absorbent composite web 60 is divided into a continuous succession of absorbent bodies 12 (FIG. 5). The transverse cut is made through the glue areas 66, so that each absorbent body 12 has two C-shaped glue areas at its opposite ends, facing the center of the absorbent body (FIG. 5).

With reference to FIG. 2, after the transverse cut, the absorbent bodies 12 are retained on the outer surface of an anvil roller 70.

Figure 6:
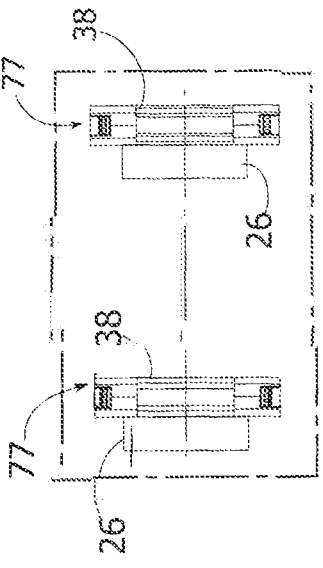
Figure 7:
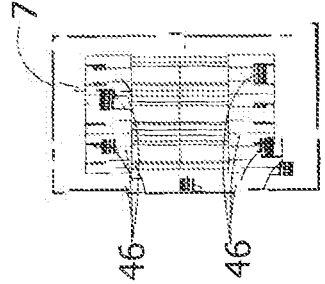

With reference to FIGS. 2 and 6, the method envisages forming a plurality of front waistbands starting from a continuous sheet 72, by means of transverse cuts made in a cut-and-slip unit 74. The front waistbands 26 at the outlet of the cut-and-slip unit 74 are held on a transfer wheel 76.

With reference to FIGS. 2 and 6, the method envisages forming a plurality of rear waistbands starting from a continuous web 78 by means of transverse cuts made in a cutting unit 80. The rear waistbands 38 at the outlet of the cutting unit 80 are applied onto the transfer wheel 76 by means of a repitch device 82.

Figure 8:
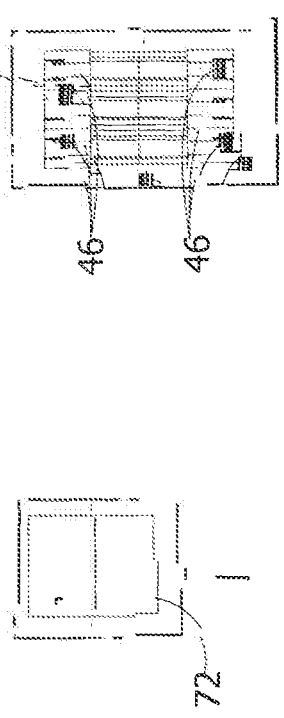

With reference to FIG. 8, on the transfer wheel 76 downstream of the repitch device 82 there are pairs of waistbands spaced apart by a distance equal to the length of the absorbent sanitary articles 10. Each pair of waistbands 77 is formed by a front waistband 26 and a rear waistband 38 adjacent to each other.

The front and rear waistbands 26, 38 arranged on the transfer wheel 76—as indicated in FIG. 8—are applied to the ends of the absorbent bodies 12 that advance on the anvil roller 70.

The front and rear waistbands 26, 38 located on the transfer wheel 76 are in phase with the absorbent bodies 12, so that a front waistband 26 is applied to each absorbent body 12 at the front transverse side 16 and a rear waistband 38 at the rear transverse side 18.

The transfer wheel 76 sequentially applies the front waistband 26 of each pair of waistbands 77 onto the inner surface 22 of a first absorbent body 12, and the rear waistband 38 of the same pair of waistbands 77 on the inner surface 22 of a second absorbent body 12 following the first absorbent body 12.

The front and rear waistbands 26, 38 are applied to the glue areas of the absorbent bodies 12 and are attached to the absorbent bodies 12 by gluing.

In a possible alternative embodiment, the front waistbands 26 and the rear waistbands 38 may be welded to the inner surface 22 of the absorbent bodies 12. The welding may be performed by ultrasonic welding or thermowelding by means of a welding unit (not shown), which can cooperate with the anvil roller 70 and is located between the transfer wheel 76 and the detachment wheel 84. In this variant, the application of glue is not envisaged.

Figure 9:
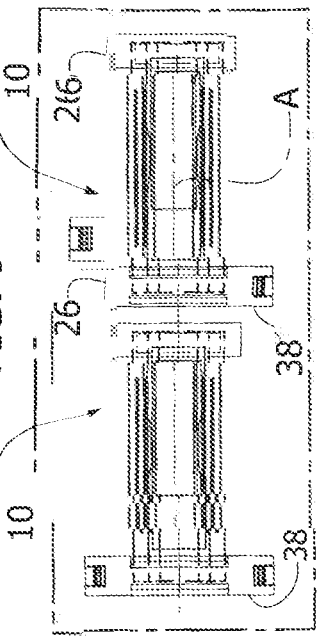

After applying the front and rear waistbands 26, 38 onto the absorbent bodies 12, the finished absorbent sanitary articles 10 are obtained. A detachment wheel 84 detaches the absorbent sanitary articles 10 from the anvil roller 70, and transfers them to an outlet conveyor 86. FIG. 9 shows the finished absorbent sanitary articles 10 in an extended position as they advance over the outlet conveyor 86.

Thereafter, the absorbent sanitary articles 10 can be folded around a central transverse axis and the side portions of the rear waistbands can be folded around longitudinal axes to bring the closing formations 46 into contact with the side portions of the front waistbands 26.

Of course, without prejudice to the principle of the invention, the details of construction and the embodiments can be widely varied with respect to those described and illustrated, without thereby departing from the scope of the invention as defined by the claims that follow.

The invention claimed is:

1. A method for producing absorbent sanitary articles, comprising:

providing a continuous absorbent composite web having a longitudinal axis and an inner surface of liquid-permeable material, advancing said continuous absorbent composite web in a machine direction parallel to said longitudinal axis, cutting said continuous absorbent composite web along a direction transverse to said longitudinal axis, so as to give rise to a continuous succession of absorbent bodies, having the inner surface and an elongated shape along said longitudinal axis, each absorbent body having two longitudinal sides, a front transverse side and a rear transverse side, forming a plurality of front waistbands from a continuous sheet of material at a first unit, and a plurality of rear waistbands from a continuous web of material at a second unit different than the first unit, the continuous web of material being different than the continuous sheet of material, each front and rear waistband having an elongated shape in the transverse direction, wherein the plurality of rear waistbands each have a greater dimension in said transverse direction than a dimension in the transverse direction of the plurality of front waistbands, the forming including cutting the continuous sheet and continuous web into respective lengths to form the respective plurality of front and rear waistbands before the front and rear waistbands are attached to an absorbent body of the continuous succession of absorbent bodies, attaching a central portion of each front waistband of the plurality of front waistbands and a central portion of each rear waistband of the plurality of rear waistbands to the inner surface of a respective absorbent body of the continuous succession of absorbent bodies while the respective absorbent body continues to have its longitudinal axis in the machine direction so that, after attaching to the respective absorbent body, each front waistband protrudes beyond said front transverse side and each rear waistband protrudes beyond said rear transverse side, applying glue areas on the inner surface of said continuous absorbent composite web at areas which will give rise to said front transverse side and to said rear transverse side, before carrying out said cut of the continuous absorbent composite web along the direction transverse to said longitudinal axis, wherein each applied glue area includes an "I" shape, with a single central portion elongated in the transverse direction and two side areas wider than the central portion extending along the longitudinal axis at opposed transverse ends of the central portion, and wherein cutting the absorbent continuous web along the direction transverse to the longitudinal axis includes cutting the absorbent continuous web through the central portion and two side portions of the applied glue areas such that after this cutting, each absorbent body includes two C-shaped glue areas at its opposite front and rear transverse sides, facing a center of the absorbent body between the front and rear transverse sides.

* * * * *

UNITED STATES PATENT AND TRADEMARK OFFICE
CERTIFICATE OF CORRECTION

| | | |
|---|---|---|
| PATENT NO. | : 12,064,324 B2 | Page 1 of 1 |
| APPLICATION NO. | : 17/075806 | |
| DATED | : August 20, 2024 | |
| INVENTOR(S) | : Gabriele Sablone | |

It is certified that error appears in the above-identified patent and that said Letters Patent is hereby corrected as shown below:

On the Title Page

(71) Applicant address information should be listed as:
- Fameccanica.Data S.p.A., San Giovanni Teatino (Chieti), ITALY -

Signed and Sealed this
Twenty-fifth Day of March, 2025

Coke Morgan Stewart
*Acting Director of the United States Patent and Trademark Office*